(12) United States Patent
Herklotz et al.

(10) Patent No.: US 6,355,363 B1
(45) Date of Patent: Mar. 12, 2002

(54) SUPPORT STRUCTURE

(75) Inventors: Günter Herklotz, Bruchköbel; Frank Krüger, Wölfersheim; Thomas Frey, Hanau; Thomas Giesel, Erlensee, all of (DE)

(73) Assignee: W. C. Hereaus GmbH & Co. KG, Hanau (DE)

( * ) Notice: Subject to any disclaimer, the term of this patent is extended or adjusted under 35 U.S.C. 154(b) by 0 days.

(21) Appl. No.: 09/504,704

(22) Filed: Feb. 16, 2000

(30) Foreign Application Priority Data

Feb. 16, 1999 (DE) .......................... 199 06 417

(51) Int. Cl.[7] .......................... A61F 2/06; A61L 29/12; C25D 3/50; C23C 28/02
(52) U.S. Cl. .................. 428/669; 428/670; 428/672; 428/681; 428/636; 604/21; 600/3
(58) Field of Search ................ 428/669, 670, 428/672, 681, 636; 604/21; 600/3

(56) References Cited

U.S. PATENT DOCUMENTS

| | | | |
|---|---|---|---|
| 5,050,606 A | * | 9/1991 | Tremulis |
| 6,059,714 A | * | 5/2000 | Armini et al. |
| 6,076,012 A | * | 6/2000 | Swanson et al. |
| 6,183,409 B1 | * | 2/2001 | Armini |

FOREIGN PATENT DOCUMENTS

| | | |
|---|---|---|
| DE | 43 28 999 A1 | 3/1995 |
| EP | 0 358 375 B1 | 8/1999 |
| JP | 06 218 060   * | 8/1994 |
| WO | WO 93/07924 | 4/1993 |
| WO | WO 93/25733 | 12/1993 |
| WO | WO 99/02195 | 1/1999 |

* cited by examiner

Primary Examiner—Deborah Jones
Assistant Examiner—Jason Savage
(74) Attorney, Agent, or Firm—Akin, Gump, Strauss, Hauer & Feld, L.L.P.

(57) ABSTRACT

A support structure is provided for holding open lumina, the support structure having a stainless steel substrate and a platinum layer forming the surface of the structure. The structure has at least one gold layer arranged between the substrate and the platinum layer. The platinum layer is preferably applied with a pulsed current with current reversal, in order to avoid or reduce brittleness occurring by absorption of hydrogen during galvanic deposition of platinum. Such a support structure (stent) substantially withstands the high mechanical stresses, particularly bending and torsional forces that occur during application, without the formation of significant tears in the platinum layer.

8 Claims, No Drawings

SUPPORT STRUCTURE

BACKGROUND OF THE INVENTION

The invention relates to a support structure to hold open lumina, having a substrate, and a support structure for holding open lumina, with a stainless steel substrate.

In medical technology it is known to use support structures to hold open lumina, so-called stents, made of stainless steel among other things. The torsional forces and bending forces upon the expansion of such stents places high demands on the mechanical properties of the material. These demands are met, as a rule, by stainless steel. However, the disadvantage of it is insufficient biocompatibility.

In addition, in EP 0 358 375 reference is made to the possibility of a platinum coating for stainless steel substrates in electronics technology that are generally not exposed to high mechanical stresses.

Further, it is known merely in electronics technology (WO 93/25733) to coat with platinum or gold and platinum structural components and substrates that are generally not exposed to high mechanical stresses.

In U.S. Pat. No. 5,824,056 a stent is disclosed which is made of a refractory metal and a biocompatible surface layer applied by sputtering, for example made of platinum.

From PCT publication WO 93/07924 a metallic or ceramic implant is known, which is coated with a thin infection-resistant, sputtered-on film.

In jewelry, which is generally also not exposed to any high mechanical stresses, a gold plating of stainless steel jewelry pieces is performed in order to increase the biocompatibility, in particular to avoid allergic skin reactions. However, in these cases the biocompatibility is also not always sufficient.

BRIEF SUMMARY OF THE INVENTION

From the above, the problem results of preparing a support structure, in particular a stainless steel support structure, which has a sufficient biocompatibility and which withstands the customarily occurring mechanical stresses, in particular upon expansion of a support structure.

This problem is solved according to the present invention by a support structure for holding open lumina, in which the structure has a substrate, a platinum layer forming the surface, and at least one gold layer arranged between the substrate and the platinum layer.

Intrinsic to the invention is first the surprising fact that the platinum layer on the stainless steel substrate withstands the mechanical stresses that occur during the application. Furthermore, it is intrinsic to the invention that surprisingly by the presence of a gold layer, which is located between a substrate, namely a stainless steel substrate, and the platinum layer, such a support structure (stent) withstands the high mechanical stresses, in particular in the form of bending and torsional forces that occur during the application, to an especially high degree without the formation of significant tears in the platinum layer.

DETAILED DESCRIPTION OF THE INVENTION

The individual layers can be applied, using known prior art processes, to the stainless steal surface of the respective support structure, in particular using sputtered-on PVD processing or using galvanic deposition.

In order to increase the mechnical stress while avoiding the above-mentioned formation of tears, it is advantageous if an additional, second gold layer is arranged between the gold layer and the platinum layer. Furthermore, the following embodiments are advantageous, since they have proven themselves in practice.

The first gold layer has a thickness of 0.01 to 0.02 $\mu$m. The second gold layer has a thickness of 0.5 to 10.0 $\mu$m. The platinum layer has a thickness of 0.1 to 1.0 $\mu$m.

In order to avoid or reduce a partial brittleness occurring by the absorption of hydrogen during the galvanic deposition of platinum, the platinum layer is applied in an advantageous way using a pulsed current with current reversal (reverse pulse plating).

In this process, cathodic and anodic current pulses are applied in alternating sequences on each workpiece that is to be platinized, in order in this way to more or less prevent any possible brittleness from occurring in the metal, by a "blasting off" of hydrogen, formed in situ, from the metal surface.

In practice, it has proven particularly useful if the cathodic pulses last 1.0 to 100 ms with a current flow density in the range from 0.5 to 10 A/dm$^2$ and if the anodic pulses last 0.1 to 10 ms with a current density in the range from 5.0 to 1,000 A/dm$^2$.

The following specific, non-limiting example serves to illustrate the invention.

A stainless steel stent is contacted with a fine wire made of gold or stainless steel (diameter approx. 100 $\mu$m) and then degreased by the process that is customary in galvanizing, e.g., cathodically or anodically in a cyanide solution. The thus-prepared stent is provided with a first gold layer (adhesive gold layer) in a hydrochloric acid gold bath (cathodic current density approx. 1–10 A/dm$^2$, layer thickness approx. 0.05 $\mu$m).

Next, a coating with a second gold layer (fine gold layer) takes place (cyanide gold bath, cathodic current density approx. 0.1–2.0 A/dm$^2$, layer thickness approx. 0.5–8.0 $\mu$m).

If the coating material is exposed in later use to a high bending stress—in the case of the stent, this is to a certain extent a given-, then the second gold layer considerably increases the tearing resistance of the occluded platinum layer.

The platinum layer can be applied with a direct current deposition as well as with a pulsed current. Baths based on, e.g., hexachloroplatinate, hexahydroxyplatinate, platinum tetramine, dinitrodiaminoplatinate, as well as sulphuric acid platinum baths can be employed for the coating. The cathodic current densities therein, depending on the bath, lie between approx. 0.5 and 2.5 A/dm$^2$. If a deposition with a pulsed current is used, then a reverse-pulse-process has proven useful, since this can act to oppose too great a hydrogen brittleness of the platinum layer. A pulse sequence in which a long cathodic pulse (1–100 ms) with a low current density (0.5–10 A/dm$^2$) is followed by a shorter anodic pulse (0.1–10 ms) with a high current density (5.0–1,000 A/dm$^2$) produced excellent results. A current pause (approx. 10–1,000 ms) prior to the repeated cathodic pulse proved useful. The exact pulse parameters must, however, be adapted to the respective stent design, since the current density distributions can vary based on screening effects.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A support structure for holding open lumina, comprising a substrate, a platinum layer forming a surface of the structure, and at least a first gold layer arranged between the substrate and the platinum layer.

2. The support structure according to claim 1, wherein a second gold layer is arranged between the first gold layer and the platinum layer.

3. The support structure according to claim 1, wherein the first gold layer has a thickness of 0.01 to 0.2 $\mu$m.

4. The support structure according to claim 2, wherein the second gold layer has a thickness of 0.5 to 10.0 $\mu$m.

5. The support structure according to claim 1, wherein the platinum layer has a thickness of 0.1 to 1.0 $\mu$m.

6. The support structure according to claim 1, wherein the platinum layer is applied by pulsed current with current reversal.

7. The support structure according to claim 6, wherein the structure is impinged during coating by pulsed current with current reversal having cathodic current pulses lasting 1 to 100 ms with a current density in the range of 0.5 to 10 $A/dm^2$.

8. The support structure according to claim 6, wherein the structure is impinged during coating by pulsed current with current reversal having anodic current pulses lasting 0.1 ms to 10 ms with a current density in the range of 5.0 to 1,000 $A/dm^2$.

* * * * *